United States Patent
VanDijk

(10) Patent No.: US 6,433,239 B1
(45) Date of Patent: Aug. 13, 2002

(54) MODIFIED CATALYST AND A METHOD OF USING SAME FOR CONVERSION OF METHANOL INTO OLEFINS

(75) Inventor: Christiaan P. VanDijk, Houston, TX (US)

(73) Assignee: Van Dijk Technologies, L.L.C., Houston, TX (US)

( * ) Notice: Subject to any disclaimer, the term of this patent is extended or adjusted under 35 U.S.C. 154(b) by 0 days.

(21) Appl. No.: 09/786,542

(22) PCT Filed: Jun. 22, 1999

(86) PCT No.: PCT/US99/14012

§ 371 (c)(1),
(2), (4) Date: Mar. 1, 2001

(87) PCT Pub. No.: WO00/01643

PCT Pub. Date: Jan. 13, 2000

Related U.S. Application Data

(60) Provisional application No. 60/091,625, filed on Jul. 2, 1998.

(51) Int. Cl.$^7$ ................................................ C07C 1/207
(52) U.S. Cl. ...................................... 585/640; 585/639
(58) Field of Search .................................. 585/639, 640

(56) References Cited

U.S. PATENT DOCUMENTS

| | | | |
|---|---|---|---|
| 4,613,720 A | 9/1986 | Bonifaz et al. | 585/640 |
| 4,698,452 A | 10/1987 | Mao et al. | 585/640 |

FOREIGN PATENT DOCUMENTS

| | | | |
|---|---|---|---|
| EP | 359841 | * | 3/1990 |

OTHER PUBLICATIONS

PCT Search Report, Oct. 19, 1999, 2 pgs.

* cited by examiner

*Primary Examiner*—Thuan D. Dang
(74) *Attorney, Agent, or Firm*—Akin, Gump, Strauss, Hauer & Feld, L.L.P.

(57) ABSTRACT

A method for converting methoxy compounds, such as methanol and dimethyl ether, into olefins, preferably ethylene, by contact with catalyst specifically prepared and/or conditioned to achieve a high yield of ethylene from the quantity of methoxy compound converted. Diffusity of the catalyst is increased by reducing it to a fine particle size and reaction conditions are controlled to ensure that less than 100% of the methoxy compound fed to a fixed bed of such catalyst is converted so as to produce a yield of ethylene of greater than 60%.

10 Claims, No Drawings

MODIFIED CATALYST AND A METHOD OF USING SAME FOR CONVERSION OF METHANOL INTO OLEFINS

CROSS-REFERENCE TO RELATED APPLICATIONS

This application relates to provisional U.S. application Ser. No. 60/091,625 filed Jul. 2, 1998.

STATEMENT REGARDING FEDERALLY SPONSORED RESEARCH

Not applicable.

BACKGROUND OF THE INVENTION

1. Field of the Invention

This invention relates to a method for converting methoxy compounds, such as methanol and dimethyl ether, into olefins, preferably ethylene, by contact with catalyst specifically prepared and/or conditioned to achieve a high yield of ethylene from the quantity of methoxy compound converted.

2. Description of the Related Art

Ethylene today is typically produced by steam cracking of a saturated hydrocarbon, such as ethane and other higher hydrocarbons or mixtures ranging from propane to naphtha and even vacuum gas oils. Ethane is a preferred feedstock since for the quantity of converted carbon the yield of ethylene is significantly higher than that of other higher olefins. Of the olefins produced by steam cracking of a saturated hydrocarbon feedstock ethylene is considered the olefin of greatest market value and hence originates the desire to maximize its production by comparison to propylene or other higher olefins.

Ethane is often available as a feedstock source only in the United States and even then its quantity is limited, and this forces foreign producers and even some U.S. producers into utilization of alternative hydrocarbon feedstocks.

This then has galvanized a search over the last 20–30 years for a viable alternative procedure for production of ethylene. In the 1970s Mobil developed a catalyst which is capable of converting methoxy compounds such as methanol and/or dimethyl ether into olefins (a MTO catalyst) and also into normally liquid saturated hydrocarbons (a MTG catalyst). The catalyst which Mobil developed is a zeolite and the most prevalently used zeolite catalyst composition has been ZSM-5. This catalyst consists of alumina and silica. Mobil describes the use of such ZSM-5 catalyst in both fixed and fluid beds for the conversion of methoxy compounds into synthetic gasoline (methanol to gasoline; MTG). Around 1980 Union Carbide researchers succeeded in building into this molecular sieve catalyst structure various amounts of phosphorus oxides. The resulting molecular sieve catalysts were called SAPO's, which letters indicate three components of these new zeolite catalysts, namely silica, alumina and phosphorus oxides. See U.S. Pat. No. 4,524,234.

Of the SAPO zeolite catalysts one specific version thereof called SAPO-34 was found to be especially effective for conversion of methanol into olefin mixtures consisting of ethylene, propylene and butylenes. Since then significant attention has been given to the possibility of producing olefins, especially ethylene, from methanol by the use of such methanol-to-olefin (MTO) catalysts.

Initial experiments with the SAPO-34 catalyst were conducted in a fixed bed reactor which produced a 100% conversion of methanol and on a converted carbon basis a yield pattern of about 50% ethylene, 30% propylene and 8% butylene with the remainder of converted carbon going to by-products and coke. See, Methanol to Olefins Process Using Silicoaluminophosphate Catalyst, presented by: Dr. Jeffery M. O. Lewis and Giacomo Corvini of Union Carbide Corporation, copyright 1988. However, quite early in the review of the possibility of using a SAPO-34 catalyst it was decided that due to coking a fixed bed operations was not attractive for commercial processing and attention switched to the possible use of this catalyst in a fluid bed operation. Use of the SAPO-34 catalyst in a fluid bed operation finally resulted in a yield pattern on a converted carbon basis of about 48% ethylene, 33% propylene, and 10% butylene. See "Gas to Olefins Using the New UOP/Hydro MTO Process" by B. V. Vora, T. L. Marker, P. T. Barger, and H. E. Fullerton of UPO, and H. R. Nilsen, S. Kvisle and T. Fuglerud of Norsk Hydro as presented to Gas Processors Association GCC Chapter, Bahrain, Nov. 22, 1995. More recently in U.S. Pat. No. 5,817,906 a yield of 53.8% ethylene 29.1% propylene and 7.8% butylene has been reported. The UOP articles reporting on this study indicate that a fluidized bed operation utilizing the SAPO-34 catalyst for production of ethylene may have an advantage over naphtha cracking, but ethane steam cracking. was admitted to still be slightly more attractive. This continued preference for ethane steam cracking has been underscored by the fact that in 1997 Union Carbide itself announced their decision to have three new ethylene plants constructed worldwide on the basis of ethane cracking. Although many researchers have tried to arrive at higher ethylene yields in a process utilizing SAPO-34 for the conversion of methanol to ethylene, these efforts have not resulted in an improved process for methanol to olefin conversion.

Accordingly, there is no commercial operation practice today that uses methanol as a feedstock for production of ethylene. This is due to many factors, such as the apparently insurmountable cap upon the yield of ethylene that can be obtained (about 50% maximum reported today) coupled with the rapid coking of a SAPO-34 catalyst which requires its employment in a fluidized bed operation since the frequency of catalyst regeneration that would appear to be necessary for a fixed bed operation appears unacceptable. See U.S. Pat. Nos. 5,817,906 and 5,095,163. Further, the reports on operations with a SAPO-34 catalyst appear to be unanimous on the fact that fresh or freshly regenerated catalyst initially gives poor yields (of ethylene), but on aging of such catalysts the yields improve markedly. This, too, mitigates against the apparent desirability of utilizing a SAPO-34 catalyst in a fixed bed operation for conversion of methanol to ethylene.

Although still a desire of the art, as yet no method of operation with a zeolite catalyst for conversion of methanol to ethylene in a high yield, greater than about 50% of the methoxy carbon content converted to ethylene, has heretofore been found.

BRIEF SUMMARY OF THE INVENTION

This invention comprises an operating method by which a zeolite catalyst for methanol to olefin conversion (a MTO catalyst) can be conditioned and used in a fixed structure mode for the conversion of methoxy compound(s) to ethylene at a very high yield of ethylene for the quantity of methoxy compound(s) reacted. The method of this invention will also minimize the quantities of propylene and butylenes produced and prolong the service time of the MTO catalyst before any regeneration is required.

A principal concept of this invention is that of an intentional balancing of the activity of an MTO catalyst particle against the diffusivity of that catalyst particle so that with a fixed mass comprising a plurality of such MTO catalyst particles, within a range of weight hourly space velocity (WHSV) practical for feeding a methoxy compound through a fixed structure comprising particles of such catalyst, production of ethylene is maximized while production of higher molecular weight olefins, such as propylene and/or butylenes, is minimized; all of this preferably while achieving a maximum conversion of such methoxy composition (70–99%) to ethylene as is consistent with these goals.

So far those materials which have been described in the art as active for catalyzing the conversion of methanol and/or dimethyl ether into olefinic hydrocarbon structures are zeolites. Such zeolites are porous or channeled structures the inlet pores of which are of a definitive range of cross-section size measurable in Angstrom units (Å). These pores and the rest of the internal surface area of the catalyst, together with the exterior boundary that defines the catalyst particle, presents a contactable surface area that has sites of atomic structure that are active points for conversion of methoxy compounds into olefinic hydrocarbon structures with a co-production of water (i.e., 2 $CH_3OH \rightarrow C_2H_4 + 2 H_2O$) and also for conversion of ethylene into higher molecular weight olefinic hydrocarbons (i.e., 3 $C_2H_4 \rightarrow 2 C_3H_6$). Such conversion of methoxy compounds and/or ethylene into other hydrocarbon structures as occurs in contact with an MTO catalyst composition occurs by reason of an appropriate contact of the reactant molecular species with a catalytically reactive site. The surface area presented by the inside surface area of such MTO catalyst compositions (hereafter inside surface area, or ISA) very greatly exceeds that surface area presented by the exterior boundaries that define a particle of such catalyst (hereafter exterior surface area, or ESA). Hence, the number of ISA active catalytic sites existing within the MTO catalyst particles greatly exceeds the number of ESA active sites existing at the boundaries of such catalyst particles.

The transport of mass into contact with the exterior surface areas (ESA) as compared to that of into contact with the inside surface area (ISA) of a catalyst particle therefore does not influence the degree and type of conversion of a methoxy reactant and also of an ethylene reactant. For all practical purposes only the ISA is the effective area of the catalyst for purposes of methoxy conversion.

Through a fixed collective structure of a multiple of such catalyst particles the amount of mass flow that can be achieved per unit of time is primarily dictated by the pressure drop between the inlet and the outlet to such structure that can practically be tolerated and this, in turn, is primarily a function of the interstitial spacing that exists between the packing of such catalyst particles in their so-fixed structure. This maximum mass flow, or any lower value therefrom, then dictates in major part the mass flow which contacts the collective exterior boundaries of the particle collective as compared to the mass that contacts the inside surface area of the particle collective, which is a function of the "diffusivity" of the feed through the inlet pores of the catalyst particles.

The diffusivity, or timed transport of mass, through the pores of a catalyst particle occurs at a much slower rate than that of the flow of mass across the exterior boundary of a catalyst particle; this because the cross-section area of a pore of the catalyst particle is much less than the interstitial spacing that exists between catalyst particles. This then means that per unit of time the degree of conversion of methanol within the catalyst particle is much greater than the degree of methanol conversion that occurs at the surface boundary of a catalyst particle. Such methanol which enters a pore inlet of a catalyst particle can become essentially completely reacted to ethylene while within the catalyst particle before this mass flow begins to approach the outlet pore of that catalyst particle. Thus, at that point within the inside surface of a catalyst particle wherein methanol has become essentially completely depleted because of its conversion to ethylene, thereafter the only mass flow toward the outlet pores is olefinic and there exists only olefins for occupancy of the catalytically active cites which remain inside the catalyst particle. This then creates a condition for the conversion of ethylene into higher olefins, such as propylene (i.e. 3 $C_2H_4 \rightarrow 2 C_3H_6$).

It is an intent of this invention that after preconditioning the MTO catalyst to achieve diffusion rates faster than the reaction rates (as evidenced by the improved performance), to then operate at such high WHSV's, that unconverted methanol to an amount of between 1 and 30% of the amount fed will be present in the effluent taken from the reactor; then the ethylene yield on basis of converted methanol will be at least more than 60%, preferably more than 70%.

Yet another aspect of this invention relates to the conditions and degree to which a catalyst that has aged during service to an unacceptable activity point is taken off line and then regenerated to an acceptable activity level. In this aspect the catalyst particle—which presumably are already of an acceptable size from the diffusivity standpoint of this invention—are only partially regenerated, but to an acceptable activity level; or if necessary to a deeper level of coke removal than is one providing for an acceptable activity level and the so deeply regenerated catalyst is thereafter pretreated under reactive conditions with propane, butane, pentane, propylene, butylene, or pentene to form a low temperature coke within the inside of the catalyst particle to balance its activity level to its diffusivity. This regeneration and/or preconditioning may be continued until the catalyst when subjected to reactive contact with a methoxy feedstock will convert at least about 90% of the methoxy compound to ethylene at at least a 60% yield.

DETAILED DESCRIPTION OF THE INVENTION

This invention comprises a specification of a preferred catalyst for conversion of methanol into olefins, together with a way to utilize this preferred catalyst as a fixed structure, as in a fixed bed process.

As a catalyst for the conversion of crude or pure methanol into olefins it is proposed to take a zeolite composition, like ZSM-5 or SAPO-34, and either made or ground down the composition to less than 1 mm maximum size, preferably less than 0.1 mm maximum size, most preferred less than 200 micron. This can be an unbound catalyst or one built into a stronger complex, preferably by combining the unbound catalyst with silica as reinforcement. In the latter case the fine catalyst has to be obtained by grinding the bound aggregate.

The very fine sized catalyst is used as such or built into a complex with high accessibility of the catalyst by the reacting gases. When used as such, materials can be added to generate space around these small catalyst particles, this to lower pressure drop. It is also possible to precipitate the catalyst on the surface of a casting having large surface area and low pressure drop structure (like the honeycomb support structure used for catalytic converters in automobiles).

It is highly preferred to use a number of parallel reactor aggregates. Each aggregate consists of a number of reactors in series. Into the first reactor the desired steam amount is fed, which is in moles between three and five times the total amount of methanol or of methoxy equivalent (i.e., DME is two methoxy) fed to the reactor-aggregate at that time.

To each of the reactors of an aggregate, methanol is fed in an amount and at a temperature, so that upon an adiabatic reaction of all the methanol present in the inlet a temperature rise in contact with the catalyst will ensue of less than 80° F., preferably less than 40° F. For the second and later reactor aligned in series the available methanol at the inlet point is the sum total of the methanol fed and the methanol left unconverted in the earlier reactor in the series. It is preferred to achieve adiabatic reaction in about the same temperature zone as in the first reactor of the series by feeding the secondary amounts of methanol at a sufficiently lower temperature, so that the heat of reaction is about equal to the amount of heat required to warm up that methanol feed. It is also possible to feed part or all of the methoxy in the form of dimethyl ether, which results in a smaller heat of reaction. Thus the control of temperature across the reactor from inlet to outlet becomes easier.

Whenever in the following the word methanol is used, it indicates use of methanol or dimethyl ether or a mixture of these compounds.

Further it is advocated to use at high initial activity of the catalyst a correspondingly high flow of both methanol and steam, preferably sized to create a minor amount of between 1 and 30%, preferably between 3 and 25%, most preferably between 5 and 20% of breakthrough of methanol or equivalent amount of dimethyl ether.

On aging of the catalyst in any reactor the flowrate of the feedstock mixture (methanol and steam) is proportionally reduced, to keep the methanol breakthrough within desired limits, as stated above. Larger amounts of methanol can be left unconverted, but then that larger amount of methanol is more difficult to recover out of the effluent of the reactor complex.

When for one reactor-aggregate the catalyst activity is reduced to an unacceptable level even at increased temperature, the methanol feed is cut out and, after a short period of sweeping out all hydrocarbons, a mixture of steam and air is fed in to regenerate the catalyst. This regeneration can be complete with a final oxidation at 500° C., or be limited to a partial regeneration, leaving between 5 and 20% of the total "coke," measured as carbon, in the catalyst.

Therefore all the aggregates are going through many cycles of reaction of methanol, sweeping out of hydrocarbons and regeneration with air. The different cycles, however, are entered into by subsequent aggregates at stepwise later times, so that an impression of the total cycle could be obtained by looking at all the aggregates at the same time. When the last aggregate is finishing a cycle to require regeneration, the first aggregate having completed regeneration is entering the start of the next cycle. The result of this staging is, that the sum total of all exit flows is relatively stable in time.

Taking a particular volume of catalyst, the reactivity of the catalyst at a given (high) activity can be assumed to be a value proportional to the total volume of the catalyst.

Assuming for simplicity the catalyst to be in spheres of equal size, the number of spheres in a given total volume of catalyst is proportional to the inverse of the third power of the radius of those spheres. The diffusion should be proportional to the outside surface area, which is proportional to the number of particles times the square of the radius. Therefore making the catalyst in small spheres increases the relative rate of diffusion over the activity by the inverse of the radius. A similar effect exists for other forms of the catalyst particles. The mathematics, however, then are more complex for mixtures of different sizes, but that can be overcome by taking certain screening procedures.

It is therefore part of the present invention to use much smaller catalyst particles. This will bring the conversion within the inside of the catalyst particles closer to the conversion as found in the gas around the catalyst particles.

This is not sufficient yet for obtaining high ethylene yields.

With the increased diffusion of a substantially smaller catalyst much more methanol can now enter per volume of catalyst. To avoid high conversion at this much increased rate, one has to feed more methanol to the new catalyst with higher conversion potential. This is necessary to avoid over-reaction of the methanol, which would lead to conversion of more and more ethylene into propylene, then into butylene and finally, most likely into coke.

It is therefore proposed to use zeolite catalysts, like ZSM-5 or SAPO-34, in the form of particles, of which the maximum size is smaller than 1 mm, preferably smaller than 0.2 mm, most preferably smaller than 0.1 mm. A screening of the fine catalyst particles can lead to a narrow size distribution, which may be preferred from handling standpoint. The thus defined small particles are to be used for the conversion of methanol, preferably in a fixed bed.

With the unusual choice of very fine catalyst the problem crops up of avoiding high pressure drops. A first helpful aspect is, that the higher catalyst activity, resulting from the substantial reduction of the diffusion barrier, leads to use of much less catalyst. Further, the low pressure, at which normally the olefin production is operated, allows more freedom in construction of the reactors. But still the pressure drop could be of considerable magnitude, so that special measures may be necessary.

The catalyst particles can be used as such or embedded into a very open structure of a on-coking medium like silica. The very open structure of the supporting structure should allow easy access by the reacting methanol. When using the small catalyst particles as such, they preferably should be used in conjunction with spacers. These spacers can be somewhat larger particles of non-reacting material, which second type particles should have a very open structure, this to lower the pressure drop in operation. It is also possible to sprinkle the catalyst particles on a woven support of fine silica fibers or in-between two layers of such a support. Tightly rolling up such a mat of support plus catalyst will provide a structure with sufficient open areas to allow a sufficiently high gas flow rate. Finally, it is also possible to precipitate the (fine) catalyst on a casting with a large number of wide channels (like a honeycomb structure used for the automobile after burner catalyst system).

In general structures should be used like large area thin beds of catalyst, which beds could be horizontal or vertical. In the last case radial flow design could be used.

It is preferred to use an excess of steam, for instance in a molar amount of between 3 and 5 to 1, preferably 4 to 1 over the total amount of methanol fed per reactor complex. The steam preferably should be fed at the inlet of the first reactor, preheated to a chosen reaction temperature like 750 to 800° F. The methanol should be added into the inlets of the different reactors of the catalyst aggregate, this to obtain adiabatic reaction within a narrow temperature zone. The methanol fed to the first bed of catalyst could be fed at the same temperature as the steam, while the methanol feeds to the following beds should be fed at a substantially lower temperature, so that the warming of the methanol can absorb the heat of reaction. Part of this methanol feed could be fed as liquid, if desired.

At the inlet of each reactor of an aggregate the mixed feed should be at a temperature of between 700 and 900° F., preferably between 725 and 825° F., while the amount of methanol present is limited to an amount that would, on complete reaction, result in a maximum temperature rise of not more than 80, preferably not more than 40° F. The amounts of methanol added into later reactors of the aggregate should likewise be limited to amounts that, together with unreacted methanol still present in the reactor at that point, will create a maximal adiabatic temperature rise of not more than 80° F., preferably not more than 40° F. It is further possible, but not necessary, that over each of the reactors of an aggregate a recycle of effluent back to the inlet of that reactor is practiced. The methanol added, especially after the first reactor, should be fed in at a sufficiently low temperature that adiabatic reaction should heat that methanol up to approximately reaction temperature.

The amount of steam and methanol fed should be varied with the activity of the catalyst at any point in time after regeneration or start of the process, which amounts are preferably sized to attain a minor amount of breakthrough of methanol or dimethyl ether. The degree of methanol left unconverted should be governed to be between 1 and 30%, preferably between 3 and 25%, most preferably between 5 and 20%. Higher conversions can be used, but a breakthrough of methanol is preferred in order to obtain high yields of ethylene. In this way the high initial activity of fresh or freshly regenerated catalyst can be used for maximized production of ethylene and the other olefins. That activity of the catalyst can be determined beforehand, allowing setting a variation in the feed rate, which will be close to achieve the desired effect.

When on any reactor aggregate the activity of the catalyst sinks below an acceptable level (for instance becomes less than 3 to 10% of the initial value), the methanol addition is stopped and the steam feeding continues until the hydrocarbons are sufficiently removed. Then the catalyst is regenerated by adding air, preferably at a temperature at or only slightly higher than the reaction temperature. After regeneration the oxygen-containing feed is stopped and the steam flow soon will make the particular reactor ready for methanol feed again.

To stabilize the output of the reaction system, a large number, like 4 to 20 parallel reactors are used, which are all stepwise sequenced, so that after the last reactor aggregate is taken out of methanol decomposition, the first reactor aggregate is regenerated and ready to start a new cycle.

Under the above conditions it is possible to increase the ethylene yield to more than 60%, under some circumstances even more than 70%, or even more than 85% of total carbon reacted as methanol. At the same time the production of olefins during a production cycle is markedly improved.

The foregoing disclosure and description of the invention are illustrative and explanatory thereof, and various changes in the details of the illustrated apparatus and construction and method of operation may be made without departing from the spirit of the invention.

What is claimed is:

1. A method for conversion of a methoxy composition at a yield of at least 60% into ethylene, comprising the steps of:
    contacting a quantity of said methoxy composition under reactive temperature conditions with a fixed structure of porous particles composed of a composition catalytically active for conversion of the methoxy composition into ethylene, said particles being of an average size in the range of 0.1 to 1 mm; and
    controlling the quantity and flow rate of said methoxy composition feed into said contact with said fixed structure of said porous particles such that following completion of contact therewith at least 1% of said methoxy composition remains as a constituent in the ethylene containing product gas composition.

2. The process of claim 1, wherein said composition catalytically active for conversion is ZSM-5 or SAPO-34.

3. The process of claim 1, wherein said composition catalytically active for conversion, prior to contact with a methoxy composition, is prereacted by a reactive condition contact with a C3–5 hydrocarbon until said composition is conditioned such that methoxy composition when contacted therewith will convert to at least 90% at a yield of at least 60% into ethylene as measured in said product gas composition.

4. The process of claim 1, wherein said catalytically active composition is one which theretofore had been in contact with a methoxy composition for a time sufficient to reduce its catalytic activity and thereafter has been only regenerated to an activity level that permits of the particles of such composition, as a fixed structure, to convert at least 90% of said methoxy composition at a yield of at least 60% into ethylene as measured in said product gas composition.

5. The process of claim 1, wherein said catalytically active composition is one which theretofore had been in contact with a methoxy composition for a time sufficient to reduce its catalytic activity and thereafter has been regenerated to an activity level that is excessive of that for the size of the particles of such composition, as a fixed structure, to convert to at least 90% of said methoxy at a yield of at least 60% into ethylene as measured in said product gas composition; and such regenerated composition is prereacted prior to a further contact with a methoxy composition by a reactive condition contact with a C3–5 hydrocarbon until said composition is conditioned such that, for the size of the particles of such composition allows for a conversion to of at least 90% thereof at a yield of at least 60% into ethylene as measured in said product gas composition.

6. The process of claim 1, wherein said methoxy composition is methanol, dimethyl ether or an equilibrium mixture thereof.

7. The process of claim 6, wherein said methoxy composition contacted with said composition catalytically activity for conversion thereof is a mixture of steam and a methoxy compound in a mole ratio of steam to methoxy compound equivalent of at least three to one and is first contacted with said catalytically active composition at a temperature of no greater than 750° F. and the product gas composition exits contact from catalytically active composition at a temperature no greater than 825° F.

8. The method of claim 1, wherein contact of methoxy composition with said composition catalytically active for conversion occurs in a series aggregate of reactor vessel(s) containing said composition, each individual reactor vessel of said aggregate being on a different HWSV for methoxy contact with the catalytically active composition therein contained so as to, with an aging of catalytically active composition therein contained, maximized the yield of ethylene from converted methoxy, until a given aggregate of reaction vessel(s) is taken off-line for catalyst regeneration while another aggregate of reaction vessel(s) previously taken off-line for catalyst regeneration is placed back into service.

9. The process of claim 8, wherein said reactor vessel(s) of said series aggregate comprises a plurality of reactor vessels in parallel.

10. The process of claim 9, wherein with regard as to said plurality of reaction vessels in parallel, the feeding of methoxy composition to the inlet of said reactor vessels occurs under conditions of temperature of said methoxy composition such that upon inlet to said vessel the methoxy composition exists at or within a temperature environment of from about 700° F. to about 900° F.

* * * * *